United States Patent
Delgado Lopez et al.

(10) Patent No.: US 10,105,390 B2
(45) Date of Patent: Oct. 23, 2018

(54) PROCESS FOR OBTAINING FLUORIDE-DOPED CITRATE-COATED AMORPHOUS CALCIUM PHOSPHATE NANOPARTICLES

(71) Applicants: Consejo Superior De Investigaciones Cientificas (CSIC), Madrid (ES); Consiglio Nazionale Delle Ricerche, Rome (IT)

(72) Inventors: Jose Manuel Delgado Lopez, Armilla (ES); Jaime Gomez Morales, Armilla (ES); Raquel Fernandez Penas, Armilla (ES); Michele Iafisco, Faenza (IT); Anna Tampieri, Faenza (IT); Silvia Panseri, Faenza (IT)

(73) Assignee: CONSEJO SUPERIOR DE INVESTIGACIONES CIENTIFICAS (CSIC), Rome (IT)

( * ) Notice: Subject to any disclaimer, the term of this patent is extended or adjusted under 35 U.S.C. 154(b) by 1 day.

(21) Appl. No.: 15/327,817

(22) PCT Filed: Jul. 21, 2015

(86) PCT No.: PCT/EP2015/066651
§ 371 (c)(1),
(2) Date: Jan. 20, 2017

(87) PCT Pub. No.: WO2016/012452
PCT Pub. Date: Jan. 28, 2016

(65) Prior Publication Data
US 2017/0209491 A1    Jul. 27, 2017

(30) Foreign Application Priority Data
Jul. 21, 2014  (ES) .................................. 201431091

(51) Int. Cl.
| | |
|---|---|
| A61K 33/42 | (2006.01) |
| A61K 8/362 | (2006.01) |
| A61K 33/16 | (2006.01) |
| A61K 31/194 | (2006.01) |
| A61Q 11/00 | (2006.01) |
| A61K 8/21 | (2006.01) |
| A61K 8/24 | (2006.01) |
| A61K 9/16 | (2006.01) |
| A61K 9/19 | (2006.01) |

(52) U.S. Cl.
CPC ............... *A61K 33/42* (2013.01); *A61K 8/21* (2013.01); *A61K 8/24* (2013.01); *A61K 8/362* (2013.01); *A61K 9/167* (2013.01); *A61K 9/1682* (2013.01); *A61K 9/19* (2013.01); *A61K 31/194* (2013.01); *A61K 33/16* (2013.01); *A61Q 11/00* (2013.01); *A61K 2800/413* (2013.01); *A61K 2800/621* (2013.01); *A61K 2800/70* (2013.01); *A61K 2800/84* (2013.01)

(58) Field of Classification Search
None
See application file for complete search history.

(56) References Cited

U.S. PATENT DOCUMENTS

2006/0110306 A1    5/2006    Chow et al.

FOREIGN PATENT DOCUMENTS

| CN | 101428779 | 5/2009 |
| JP | 2001169121 | 6/2001 |
| WO | WO 98/40406 | 9/1998 |
| WO | WO 03/059304 | 7/2003 |

OTHER PUBLICATIONS

Combes et al., *Amorphous calcium phosphates: Synthesis, properties and uses in biomaterials*, 6(9) Acta Biomaterialia 3362-3378 (2010).
Delgado-López et al., *Crystallization of bioinspired citrate-functionalized nanoapatite with tailored carbonate content*, 8 Acta Biomaterialia 3491-3499 (2012).
Dorozhkin, *Amorphous calcium (ortho)phosphates*, 6 Alta Biomaterialia 4457-4475 (2010).
Dorozhkin, *Nanosized and nanocrystalline calcium orthophosphates*, 6 Acta Biomaterialia 715-734 (2010).
Zhao et al., *Amorphous calcium phosphate and its application in dentistry*, 5(40) Chemistry Central Journal 1-7 (2011).
Li, *Crystalline behaviors of hydroxyapatite in the neutralized reaction with different citrate additions*, 192 Powder Technology 1-5 (2009).
Stanic et al., *Synthesis of fluorine substituted hydroxyapatite nanopowders and application of the central composite design for determination of its antimicrobial effects*, 290 Applied Surface Science 346-352 (2014).

*Primary Examiner* — Johann R Richter
*Assistant Examiner* — Katherine Peebles
(74) *Attorney, Agent, or Firm* — Buchanan Ingersoll & Rooney PC

(57) ABSTRACT

Process for obtaining fluoride-doped citrate-coated amorphous calcium phosphate nanoparticles. This material has applications in biomedicine due to its biodegradability and bioactivity; it also promotes cell adhesion and osteogeneration. In dentistry, it may be used in toothpastes, mouthwashes, chewing gums, gels and fluoride varnishes as a remineralising agent of dentine and enamel. It is based on two solutions formed by calcium chloride and sodium citrate on the one hand, and by sodium monohydrogenophosphate and sodium carbonate with a fluoride compound on the other, which are mixed at room temperature. The process is eco-efficient and eco-friendly, as it does not leave any acid residue; it consists of a single stage and it is the first time that an amorphous calcium phosphate coated with citrate and doped with fluoride, which enhances its remineralising action, is obtained.

11 Claims, 3 Drawing Sheets

PROCESS FOR OBTAINING FLUORIDE-DOPED CITRATE-COATED AMORPHOUS CALCIUM PHOSPHATE NANOPARTICLES

CROSS-REFERENCE TO RELATED APPLICATIONS

This application is a U.S. National Stage Application pursuant to 35 U.S.C. § 371 of International Patent Application PCT/EP2015/066651, filed on Jul. 21, 2015, and published as WO 2016/012452 on Jan. 28, 2016, which claims priority to Spanish Patent Application P 201431091, filed on Jul. 21, 2014, all of which are incorporated herein by reference in their entireties for all purposes.

SECTOR AND OBJECT OF THE INVENTION

Biomaterials of interest in biomedicine (i.e., drug delivery nanocarriers and bone regeneration) and dentistry.

The object of the invention is a process for obtaining amorphous calcium phosphate nanoparticles coated with citrate (a molecule that forms part of the organic phase of the bone) and doped with fluoride. This material has a wide range of applications in the field of biomedicine (i.e. drug delivery nanocarriers and bone regeneration) due to its excellent biodegradability and bioactivity, in addition to promoting cell adhesion and osteogeneration. Likewise, it has multiple applications in dentistry, where it may be used in toothpastes, mouthwashes, fluoride varnishes, chewing gum and gels as a remineralising agent of dentine and enamel.

The process is based on two solutions formed by calcium chloride and sodium citrate on the one hand, and sodium monohydrogenophosphate and sodium carbonate with a fluoride compound on the other, which are mixed at room temperature. With respect to the prior art, it has the advantages that the process is eco-efficient, and eco-friendly since it does not leave any acidic residue (strong acids are not used in the synthesis), it is synthesised in a single stage (on using the sodium citrate as a reactive agent in the synthesis) and it is the first time that a citrate-coated and fluoride-doped amorphous calcium phosphate is obtained, therefore with a stronger remineralising action than amorphous calcium phosphate.

STATE OF THE ART

The amorphous phase is a less frequent form of mineral calcium phosphate (CaP) in living organisms. Amorphous calcium phosphate (ACP) has been found in the mitochondria of eukaryotic and prokaryotic cells and is considered the precursor stage in the formation process of the mineral phase of bone, nanocrystalline carbonate-apatite. The surface of this bone apatite has recently been found to be coated with citrate. ACP also acts as an intermediate phase in the preparation of various CaPs using different methods. This material has a wide range of applications in the field of biomedicine due to its interesting properties such as excellent bioactivity, facilitates cell adhesion and also favours osteoconductivity and osteogeneration. Likewise, it has multiple applications in dentistry, where it may be used in toothpaste, mouthwashes, chewing gum, gels and fluoride varnishes as a remineralising agent of dentine and enamel.

WO98/40406 discloses a product composed of amorphous calcium phosphate stabilised with casein, a phosphoprotein present in milk. This product is currently used as an abrasive material in toothpastes, chewing gum and in tooth whitening post-treatments. However, its efficiency in preventing caries and remineralising damaged varnish has not yet been demonstrated. ACP is also used in compound polymeric materials as a filler material in the preparation of dental pieces. ACP stimulates tooth repair particularly due to the fact that Ca and phosphate ions are released in response to acid pHs generated by bacterial plaque, which are deposited on the tooth structure in the form of hydroxyapatite, regenerating enamel (mainly composed of crystalline hydroxyapatite). Table 1 summarises the main applications of ACP as a biomaterial.

TABLE 1

Amorphous calcium phosphates used as biomaterials.

| Type of material | Application | Effect |
|---|---|---|
| Cements | Bone replacement Dentistry | Hardening agent Absorbable with high surface reactivity Source of $Ca^{2+}$ and $PO_4^{3-}$ ions |
| Coatings | Metallic protheses | Increases biodegradability and its biological activity |
| Mineral/organic compounds | Tooth remineralisation Bone replacement | Improves its mechanical properties Release of $Ca^{2+}$ and $PO_4^{3-}$ ions, increasing their biological activity |
| Aqueous suspension | Release of genes | Absorbable and biocompatible pH-dependent stability |

Some of these applications are described in J. Zhao et al., *Amorphous calcium phosphate and its application in dentistry*; Chemistry Central Journal (2011), 5:40 (doi:10.1186/1752-153X-5-40).

As regards the preparation of ACP, it is known in several modalities obtained from soluble $Ca^{2+}$ and $PO_4^{3-}$ precursors at adequate pHs for precipitation, commonly using soluble precursors whose cation does not give rise to other species that could interfere a posteriori in the composition of the final product, such as $Ca(OH)_2$, $H_3PO_4$, phosphate or ammonium hydrogenophosphate. $Ca(NO_3)_2$ is frequently used.

The function of citric acid as a $Ca^{2+}$ cation complexer is also known, which is also acceptable from the pharmaceutical viewpoint, in addition to, for example, other polycarboxylic acids such as tartaric acid. For this reason, these acids are also used to stabilise amorphous compositions of ACP. This is set out in the claims of publication WO03059304, where citric acid is proposed, among other chelate formers with the $Ca^{2+}$ cation, in the proportion 0.1% to 5% by weight in a preparation containing ACP combined with a phosphopeptide.

JP2001169121 proposes the use of citric acid as a stabiliser of ACP already formed by precipitation from phosphoric acid and calcium hydroxide, subjecting it to subsequent milling in the presence of the aforementioned citric acid.

Therefore, none of these publications mentions a preparation such as the process object of the present invention, in which citrate is added as a reactive agent for ACP precipitation (in a single-stage process) and not as a stabiliser in a phase subsequent to precipitation (two-stage process).

The revisions performed by Dorozhkin S. V. [*Nanosized and nanocrystalline calcium orthophsphates*, Acta Biomaterialia (2010), No. 6 (3), 715-734]; Cornbes C. and Rey C.

[*Amorphous calcium phosphates: synthesis, properties and uses in biomaterials*, Acta Biomaterialia (2010), No. 6 (9), 3362-3378] and another revision by Dorozhkin S. V. [*Amorphous calcium phosphates*, Acta Biomaterialia (2010), No. 6 (12), 4457-4475 disclose several wet processes, but in which the same conditions, process stages and reactive agents of the process object of the present invention are not applied. In fact, citric acid is often envisaged as a dispersant agent in these preparations and occasionally the carbonate anion, with similar functions.

The publication of J. M. Delgado-López et al. *Crystallization of bioinspired citrate-functionalized nanoapatite with tailored carbonate content* (Acta Biomaterialia (2012) No. 8, page 3491) establishes an apatite and a citrate-coated nanocrystalline carbonate-apatite precipitation process. The substantial differences in the state of the art between the process object of the present invention and this document are as follows:

(1) Precipitation temperature.
(2) Precipitation of citrate-coated and fluoride-doped ACP nanoparticles as a stable phase.
(3) There is no maturity process of the precipitate.
(4) Apatite or any other crystalline phase of the calcium phosphate is not formed in the precipitate.

BRIEF DESCRIPTION OF THE INVENTION

A first object of the present invention is a process for obtaining fluoride-doped citrate-coated amorphous calcium phosphate (FACP) comprising:
  the preparation of a $CaCl_2$ solution at a concentration comprised between 0.08 M and 0.12 M and $Na_3C_6H_5O_7$ (sodium citrate) at a concentration comprised between 0.35 M and 0.50 M;
  the preparation of a second solution formed by $Na_2HPO_4$ at a concentration comprised between 0.10 M and 0.15 M with $Na_2CO_3$ 0.2 M and a fluoride compound;
  mixture under stirring of the two solutions prepared in the previous stages in the proportion 1:1 v/v at a pH comprised between 8.3 and 8.7 (adjusted, for example, with HCl) and at room temperature for a time period of less than 2 minutes;
  three successive sedimentation cycles by centrifugation, removal of the supernatant and washing of the precipitate with ultrapure water; and
  freeze-drying of the wet precipitate.

In a preferred embodiment of the invention, the concentrations of the reactive agents used in the first solution are 0.1 M for $CaCl_2$ and 0.4 M for $Na_3C_6H_5O_7$ and the concentrations used for the second solution are 0.12 M for $Na_2HPO_4$ and 0.2 M for $Na_2CO_3$.

The fluoride compound is selected from among $CaF_2$, NaF or KF and is added to a concentration comprised between 0.01 M and 0.1 M. In a preferred embodiment, the fluoride compound is $CaF_2$ and is added to a concentration of 0.05 M.

Another object of the present invention is constituted by fluoride-doped amorphous calcium phosphate nanoparticles obtained by the previous process, having a spherical shape and size comprised between 30 nm and 80 nm, as well as the following Na, Ca, P, citrate, carbonate, fluoride and structural water content comprised:
  between 3.1% and 3.5% by weight of Na
  between 27.0% and 27.4% by weight of Ca
  between 37.0% and 37.8% by weight of P
  between 3.5% and 5.0% by weight of citrate
  between 5.4% and 7.0% by weight of carbonate
  between 6% and 10% by weight of water
  between 2% and 5% by weight of fluoride The term "water" relates in this aspect of the invention both to adsorbed water and structural water.

In a third aspect, another object of the invention is the use of nanoparticles in applications such as:
  transport of biomolecules and/or drugs
  biomaterials in orthopaedic applications
  in dentistry, preferably as a material for preparing cements for filling and/or sealing root Canals and dental repairs, or as a component of toothpastes, chewing gums, mouthwashes, fluoride varnishes and gels to favoring the remineralisation of enamel through the gradual release of calcium, phosphate and fluoride ions.

EMBODIMENT OF THE INVENTION

Figure 1:
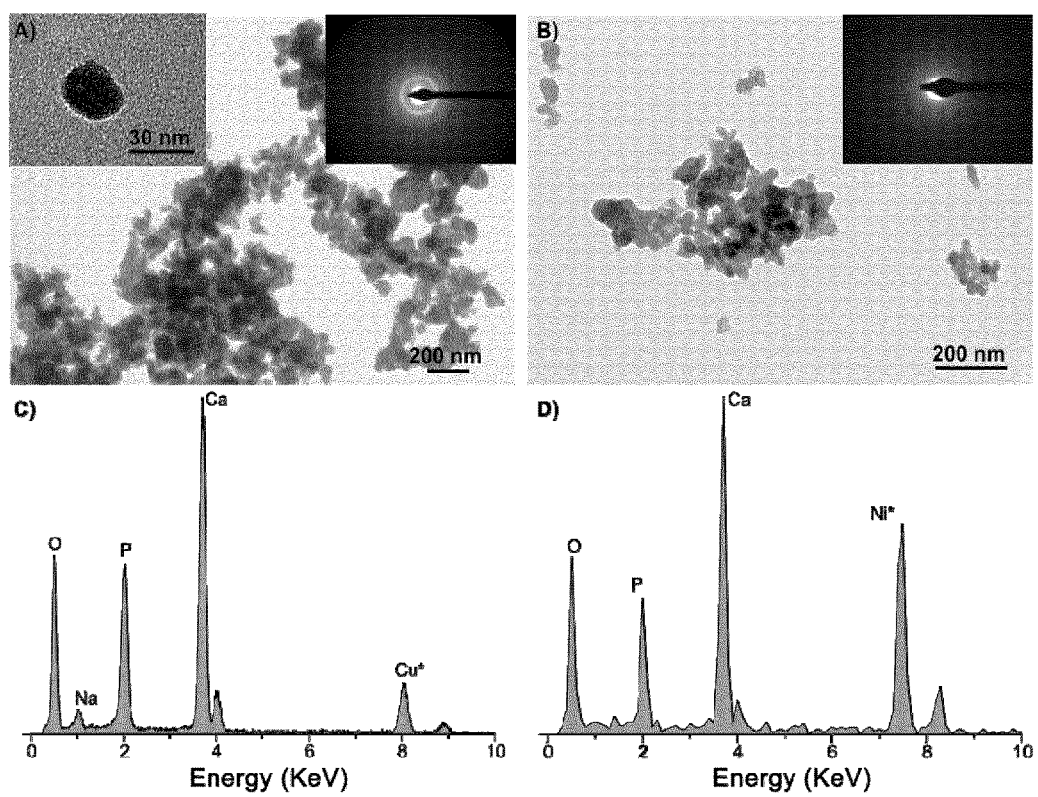
FIG. 1 shows transmission electron microscopy (TEM) images of the citrate-coated ACP (a) and FACP (b) nanoparticles. The selected area electron diffraction patterns (SAED) obtained for each of the nanoparticles are also shown as insets. The left inset in A shows a TEM image of a single nanoparticle. Panels c and d represent ACP and FACP X-ray energy dispersive (EDS) spectra, respectively.

ACP nanoparticles were obtained by a precipitation process by mixing two solutions containing:
  (i) 0.1 M $CaCl_2$+0.4 M $Na_3C_6H_5O_7$ and
  (ii) 0.12 M $Na_2HPO_4$+0.2M $Na_2CO_3$
in the proportion 1:1 v/v, a total of 200 ml and adjusting the pH to 8.5 with HCl at ambient temperature.

When the mixture takes on a milky appearance (approximately 30 s after mixing), the particles are subjected to three successive sedimentation cycles by centrifugation, removal of the supernatant and washing of the precipitate with ultrapure water (MilliQ©, Millipore). Subsequently, the wet precipitate is freeze-dried and the particles are subsequently characterised.

In order to obtain these fluoride-doped particles, $CaF_2$ 0.05 M is added to the solution (ii).

Characterisation Techniques

The nanoparticles were analysed using a Scanning Transmission Electron Microscope (STEM Philips CM 20) operating at 80 kV. This equipment also allowed the acquisition of selected area electron diffraction (SAED) patterns and X-ray energy dispersive (EDS) spectra. For these analyses, the freeze-dried samples were dispersed in ultrapure water and then a few drops of this suspension were deposited on conventional copper gratings.

The amount of Ca and P was quantified using optical emission spectroscopy (ICP-OES) using a Liberty 200 (Varian, Australia) spectrometer. To this end, the freeze-dried samples were dissolved in concentrated ultrapure nitric acid (1% v/v).

The thermogravimetric analysis (TGA) was performed using a SDT Q 600 system (TA Instruments, New Castle, Del., USA) under a constant flow of nitrogen (100 mL·min$^{-1}$) and increasing the temperature up to 1,200° C. at intervals of 10° C.·min$^{-1}$.

The X-ray diffraction patterns were acquired using an X-Pert PRO (PANalytical) diffractometer equipped with a PIXcel detector operating at 45 kV and 40 mA, with incident Cu Kα radiation (A=1,5418 Å). Variable spectral bandwidths (anti-scatter) having a radiation length of 10 mm were used. The 2θ range was varied from 5° to 70° with increments in 2θ of 0.039.

The Raman spectra were obtained using a LabRAMHR spectrometer (Jobin-Yvon, Horiba, Japan). This unit is equipped with a diode laser as an excitation source (λ=532 nm) and a Peltier-cooled CCD detector (1026×256 pixels). The spectra were obtained with a spectral resolution of 3 cm$^{-1}$.

The quantity of fluoride in the samples was quantified by X-ray fluorescence spectroscopy (XRF) using a PHILIPS Magix Pro (PW-2440) spectrometer. Additionally, the fluoride content was also determined by spectrophotometry complexed with zirconyl chloride and eriochrome cyanine R and measuring the absorbance of the complex at 570 mm.

Analysis of In Vitro Cell Culture

The biological response of the nanoparticles was evaluated using human osteoblast cell lines (MG-63, Lonza, Italy). The cells were cultured in DMEM/F12 medium (PAA, Austria), containing 10% of fetal bovine serum (FBS) and streptomycin-penicillin (100 U/mL-100 μg/mL) at 37° C. and in a $CO_2$ atmosphere (5%). Subsequently, the cells were separated from their medium by trypsinisation and then centrifuged and resuspended. The Trypan blue exclusion test was used to count the live cells (cell viability test). The cells were deposited on 96-well plates with a density of 3.0×10$^3$ cells per well. Twenty-four hours later, three different concentrations of citrate-coated ACP nanoparticles were added to the cell culture (100 μg/mL, 500 μg/mL, 1,000 μg/mL), previously sterilized by 25 kGy γ radiation. The cells were incubated under standard conditions (37° C., 5% $CO_2$) for 1, 3 and 7 days. The culture medium was renewed every three days. All these assays were conducted in a laminar flow cabinet.

MTT Cytotoxicity and Cell Viability

The MTT method [3-(4.5-dimethylthiazol-2-yl)-2.5-diphenyltetrazolium bromide] was used to determine the possible toxic effect of the nanoparticles. This assay is based on the metabolic reduction of 3-(4.5-dimethylthiazol-2-yl)-2.5-diphenyltetrazolium bromide (MTT) by the mitochondrial enzyme succinate dehydrogenase in a blue-coloured compound (formazan), whose concentration may be colorimetrically determined, making it possible to determine the mitochondrial functionality of the treated cells.

The cells, after being in contact with the nanoparticles for 1, 3 and 7 days, were incubated in MTT dissolved in PBS (5 mg mL$^{-1}$) in the proportion 1:10 for 2 hours at 37° C. The cells were then incubated with 200 μl of dimethyl sulfoxide (Sigma) for 15 min to dissolve the formazan crystals. A Multiskan FC Microplate (Thermo Scientific) spectrometer was used to measure absorbance, which is directly proportional to the number of metabolically active cells, at 570 nm. Three samples were analysed for each of the time intervals studied (1, 3 and 7 days).

Results

Figure 2:
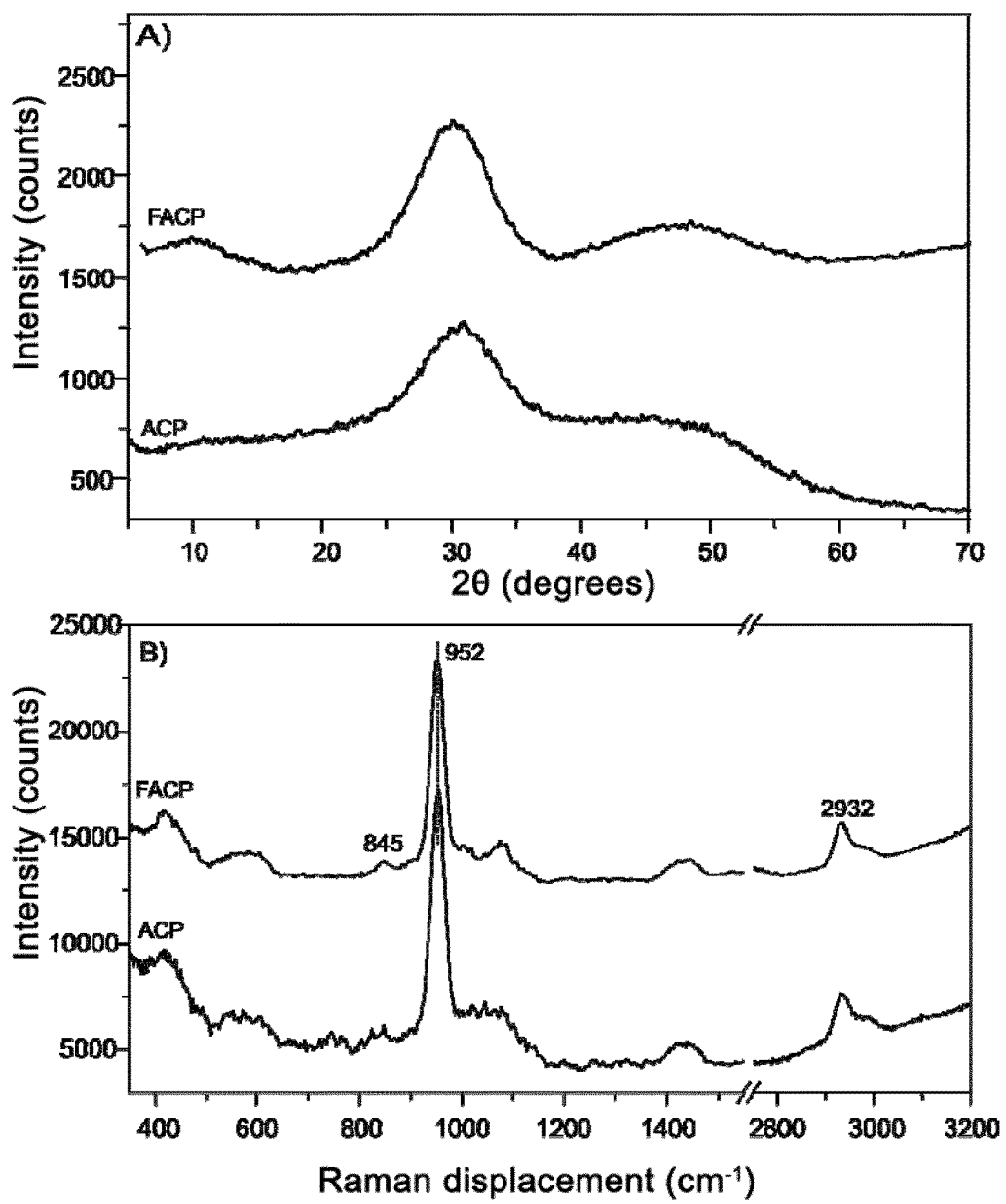
FIG. 2 shows nanoparticles X-ray diffractograms (a) and Raman spectra (b).

TEM images (FIG. 1) indicate that both the non-doped samples, ACP (A), and doped samples, FCAP (B), are spherical nanoparticles with sizes comprised between 30 nm and 80 nm. Also, the absence of diffraction points in the SAED patterns evidences their amorphous nature. In turn, the EDS spectra confirm that they are composed only of Ca and P. The F peak in the doped particle spectrum that should appear around 0.68 KeV is not observed, possibly because it is overlapped by the oxygen peak (0.2 KeV), which is by far more intense. The absence of peaks in the X-ray diffraction patterns confirms the amorphous nature of these materials (FIG. 2A). Raman spectra are also typical of amorphous calcium phosphates, as the main peak appears at 952 cm$^{-1}$, slightly shifted with respect to the main crystalline hydroxyapatite peak (961 cm$^{-1}$). The chemical composition of the ACP and FACP materials obtained by TGA, ICP and X-ray fluorescence has already been described earlier.

Figure 3:
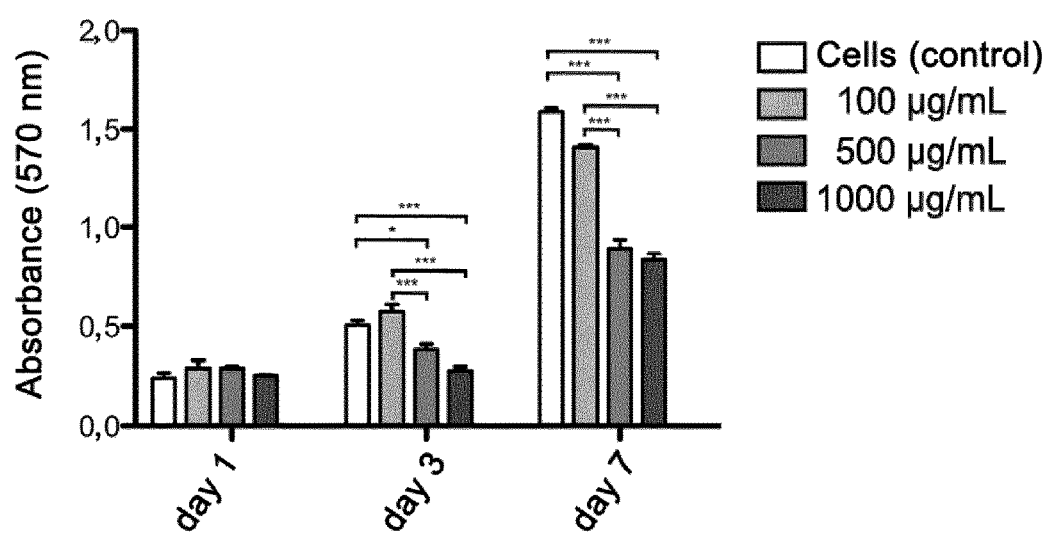
FIG. 3 shows MTT cell proliferation assays conducted on human osteoblasts incubated for 1, 3 and 7 days with ACP nanoparticles (100 µg/mL, 500 µg/mL, 1,000 µg/mL). *p 0:05; ***p 0:001; n=3.

The biological response of the nanoparticles was studied using osteoblast cells (MG-63). Three different nanoparticle concentrations (100, 500 and 1,000 μg/ml) were added to the culture medium and, after a certain incubation period (1, 3 or 7 days), the number of metabolically active cells was quantified by MTT assays (FIG. 3). An increase in cell proliferation was observed in all cases (even for the highest concentration) after 1 to 7 days of incubation. Also, for the lowest concentration studied, cell growth is comparable to that observed by the cells in the absence of nanoparticles (control). However, increasing the concentration, cell growth is much less significant than in the control, possibly due to the fact that they are excessively high nanoparticle concentrations. Despite this, the cell viability and morphology assays (not shown) obtained very similar results for all the concentrations studied. These results clearly indicate that the nanoparticles are completely biocompatible in contact with this human osteoblast cell line.

The invention claimed is:

1. A process for obtaining fluoride-doped citrate-coated amorphous calcium phosphate nanoparticles comprising:
    preparing a first solution comprising $CaCl_2$ at a concentration comprised between 0.08 M and 0.12 M and $Na_3C_6H_5O_7$ at a concentration comprised between 0.35 M and 0.50 M;
    preparing a second solution comprising $Na_2HPO_4$ at a concentration comprised between 0.10 M and 0.15 M, $Na_2CO_3$ at a concentration of 0.2 M and a fluoride compound;
    mixing under stirring the two solutions prepared in the previous stages in the proportion 1:1 v/v at a pH comprised between 8.3 and 8.7 at ambient temperature for a time period of less than 2 minutes;
    performing three successive sedimentation cycles of the mixture of the two solutions formed in the previous step by centrifugation, removal of the obtained supernatant and washing of the obtained precipitate using ultrapure water; and
    freeze-drying the wet precipitate obtained in the previous step.

2. The process according to claim 1, characterised in that the concentrations used for the first solution are 0.1 M for $CaCl_2$ and 0.4 M for $Na_3C_6H_5O_7$.

3. The process according to claim 1, characterised in that the concentrations used for the second solution are 0.12 M for $Na_2HPO_4$ and 0.2 M for $Na_2CO_3$.

4. The process according to claim 1, characterised in that the fluoride compound is selected from among $CaF_2$, NaF and KF and is added to a concentration comprised between 0.01 M and 0.1 M.

5. The process according to claim 4, characterised in that the fluoride compound is $CaF_2$ which is added to a concentration of 0.05 M.

6. Citrate-coated and fluoride-doped amorphous calcium phosphate nanoparticles obtained by a process comprising:

preparing a first solution comprising $CaCl_2$ at a concentration comprised between 0.08 M and 0.12 M and $Na_3C_6H_5O_7$ at a concentration comprised between 0.35 M and 0.50 M;

preparing a second solution comprising $Na_2HPO_4$ at a concentration comprised between 0.10 M and 0.15 M, $Na_2CO_3$ at a concentration of 0.2 M, and a fluoride compound;

mixing under stirring the two solutions prepared in the previous stages in the proportion 1:1 v/v at a pH comprised between 8.3 and 8.7 at ambient temperature for a time period of less than 2 minutes;

performing three successive sedimentation cycles of the mixture of the two solutions formed in the previous step by centrifugation, removal of the obtained supernatant and washing of the obtained precipitate using ultrapure water; and freeze-drying the wet precipitate obtained in the previous step, characterised in that they have a spherical shape and a size comprised between 30 nm and 80 nm and sodium, calcium, and phosphate, citrate, carbonate, fluoride and water content comprised:

between 3.1% and 3.5% by weight of sodium
between 27.0% and 27.4% by weight of calcium
between 37.0% and 37.8% by weight of phosphate (P)
between 3.5% and 5.0% by weight of citrate
between 5.4% and 7.0% by weight of carbonate
between 6% and 10% by weight of water, and
between 2% and 5% by weight of fluoride.

7. A vehicle for biomolecules, drugs, or both comprising the citrate-coated and fluoride-doped amorphous calcium phosphate nanoparticles as defined in claim 6.

8. A biomaterial comprising the fluoride-doped citrate-coated amorphous calcium phosphate nanoparticles as defined in claim 6.

9. The biomaterial according to claim 8, wherein the biomaterial is orthopaedic or dental.

10. A composition comprising the citrate-coated and fluoride-doped amorphous calcium phosphate nanoparticles as defined in claim 6.

11. The composition according to claim 10, wherein the composition is toothpaste, chewing gum, mouthwash, fluoride varnish, or gel.

* * * * *